(12) United States Patent
Gokaraju et al.

(10) Patent No.: US 8,524,769 B2
(45) Date of Patent: Sep. 3, 2013

(54) PROCESS FOR PRODUCING A FRACTION ENRICHED UP TO 100% OF 3-O-ACETYL-11-KETO-BETA-BOSWELLIC ACID FROM AN EXTRACT CONTAINING A MIXTURE OF BOSWELLIC ACIDS

(75) Inventors: Ganga Raju Gokaraju, Andhra Pradesh (IN); Rama Raju Gokaraju, Andhra Pradesh (IN); Venkata Subbaraju Gottumukkala, Tirupati (IN); Trimurtulu Golakoti, Andhra Pradesh (IN); Sridhar Pratha, Andhra Pradesh (IN)

(73) Assignee: Laila Impex, Vijayawada (IN)

( * ) Notice: Subject to any disclaimer, the term of this patent is extended or adjusted under 35 U.S.C. 154(b) by 1437 days.

(21) Appl. No.: 10/432,058

(22) PCT Filed: Mar. 5, 2002

(86) PCT No.: PCT/IN02/00034
§ 371 (c)(1),
(2), (4) Date: May 16, 2003

(87) PCT Pub. No.: WO03/074063
PCT Pub. Date: Sep. 12, 2003

(65) Prior Publication Data
US 2004/0073060 A1 Apr. 15, 2004

(51) Int. Cl.
*A61K 31/21* (2006.01)
(52) U.S. Cl.
USPC .......................................................... 514/510
(58) Field of Classification Search
USPC ................................................ 514/766, 510
See application file for complete search history.

(56) References Cited

U.S. PATENT DOCUMENTS

| | | | | |
|---|---|---|---|---|
| 4,725,588 | A * | 2/1988 | Snyder et al. | 514/114 |
| 5,212,323 | A * | 5/1993 | Mashiba et al. | 549/389 |
| 5,629,351 | A * | 5/1997 | Taneja et al. | 514/765 |
| 6,147,088 | A * | 11/2000 | Goulet et al. | 514/312 |
| 2003/0199581 | A1 | 10/2003 | Seligson et al. | |

OTHER PUBLICATIONS

Pardhy et al., Indian Journal of Chemistry, vol. 16B, pp. 176-178, 1978.*
Sailer et al., "Acetyl 11-keto-beta-boswellic acid (AKBA): structure requirements for binding and 5-lipoxygenase inhibitory activity.", British Journal of Pharmacology, vol. 117, p. 615-618, 1996.*
Goodman and Gilman, 7th edition, pp. 44-45, 1985.*
Pardy, R.S., et al.; "β-Boswellic Acid, Acetyl-β2-boswellic Acid, Acetyl-II-keto-β-boswellic Acid & II-Keto-β-boswellic Acid, Four Pentacyclic Triterpene Acids from the Resin of *Boswellia serrata* Roxb," *Indian Journal of Chemistry*, vol. 16B, pp. 176-178 (Mar. 1978).

* cited by examiner

*Primary Examiner* — Barbara P Badio
(74) *Attorney, Agent, or Firm* — Kramer / Amado, P.C.

(57) ABSTRACT

The invention relates to a process for producing a fraction enriched upto 100% of 3-O-acetyl-11-keto-β-boswellic acid. An organic solvent extract of gum resin from *Boswellia* species is first subjected to oxidation and then acetylation or vice versa. This converts the less potent boswellic acids present in the fraction to AKBA. This treated fraction is subjected to further purification and separation by chromatographic separation techniques to enhance its purity and to remove contaminants therefrom. This process provide an access to a fraction enriched in 10-100% AKBA for therapeutic applications.

17 Claims, 2 Drawing Sheets

11-keto-β-boswellic acid (B1)

3-O-acetyl-11-keto-β-boswellic acid (AKBA, B2)

α-boswellic acid (B3)

β-boswellic acid (B4)

3-acetyl-α-boswellic acid (B5)

3-acetyl-β-boswellic acid (B6)

PROCESS FOR PRODUCING A FRACTION ENRICHED UP TO 100% OF 3-O-ACETYL-11-KETO-BETA-BOSWELLIC ACID FROM AN EXTRACT CONTAINING A MIXTURE OF BOSWELLIC ACIDS

This application is a 371 of PCT/IN02/00034 filed Mar. 5, 2002.

FIELD OF INVENTION

This invention relates to a process for producing a fraction enriched upto 100% of 3-O-acetyl-11-keto-β-boswellic acid from an extract containing a mixture of boswellic acids.

BACKGROUND OF THE INVENTION

Gum resin of *Boswellia* species known as frankincense has been used as an anti-inflammatory agent in Traditional Ayurvedic Medicine in India. Studies carried out have established anti-inflammatory activity of an alcoholic extract of the gum resin obtained from *Boswellia serrata* in mice and rats. This extract is also shown to inhibit the formation of leukotrienes in rat peritoneal neutrophils in vitro. The source of anti-inflammatory actions has been attributed to boswellic acids (Safayhi, H., et al., *Planta Medica* published from USA and 63 487-493, 1997; *J. Pharmacol and Exp. Ther.,* 261, 1143-46, 1992) published from USA, a group of triterpene acids isolated from the *Boswellia* resin (Pardhy, R. S., et al., *Indian J. Chem,* 16B, 176-178, 1978). These compounds exert anti-inflammatory activity by inhibiting 5-lipoxygenase (5-LO), a key enzyme for the biosynthesis of leukotrienes and 5(S)-HETE from arachidonic acid. A detailed study on the structure requirements for boswellic acids indicated that of all the six acids, 3-O-acetyl-11-keto-β-boswellic acid, hereinafter referenced as AKBA shows most pronounced inhibitory activity (Sailer, E. R., et al., *British J. Pharmacology,* 117, 615-618, 1996). AKBA acts by a unique mechanism, in which it binds to 5-LO in a calcium-dependent and reversible manner and acts as a non-redox-type, non-competitive inhibitor (Sailer, E. R., et al., *Eur. J. Biochem.* 256, 364-368. 1998).

Gum resin of *Boswellia* and boswellic acids have been known to possess other therapeutic activities and they are being used to treat human ailments such as bronchial asthma (Gupta I. et al, *Eur. J. Med. Res.,* 3(11), 511-514, 1998), ulcerative colitis (Gupta, I., Parihar, A., et al, *Eur. J. Med. Res.* 2(1), 3743, 1997) and human leukemia (Yu Shao, Chi-Tang Ho et al, *Planta Medica* published from USA, 64, 328-331, 1998). Anticarcenogenic property of alcoholic extract of this resin has been disclosed by Mukherji, S., et al (*Indian J. Pharma.,* 32, 48-49, 1970). Immunomodulatory activity of boswellic acids had been reported by Sharma et al in *Phytotheraphy Research,* (10, 107-112, 1996), published from USA.

DISCLOSURE OF THE INVENTION

Organic solvent extract of the gum resin of *Boswellia serrata* is found to contain a total of six boswellic acids. These acids are shown in FIG. 1 and are represented by B1, B2, B3, B4, B5 and B6. Concentration of AKBA, indicated as B2 in the FIG. 1, amounts only in the range of 1 to 10% in the natural boswellic acids fraction.

Present invention is aimed at enriching the concentration of AKBA in the boswellic acids fraction to a desired concentration upto 100%. Another objective of this invention is to remove inactive or less potent boswellic acids by converting them to highly potent AKBA. It is possible to obtain AKBA of high purity upto 100% by the simple process followed by the inventors.

A combination of chemical reactions and physical separations by chromatographic methods achieves these objectives.

The first step in the process involves the oxidation of the boswellic acid mixture to keto-boswellic acids. An oxidant conventionally used for allylic oxidation is preferably used for this step. The second step involves conversion of 11-keto-β-boswellic acids obtained from oxidation to 3-O-acetyl-11-keto-β-boswellic acid by acetylation. Dry material obtained after acetylation showed 30-40% AKBA by HPLC analysis.

Alternately, the first step in the process involved acetylation of the boswellic acids mixture to acetylated boswellic acids. This step could be executed by any typical acetylating agent like acetic anhydride/pyridine. The second step involves conversion of acetylated boswellic acids into 3-O-acetyl-11-keto-β-boswellic acid by oxidation. Oxidizing agents such as selenium dioxide in a suitable solvent, sodium dichromate AcOH—$Ac_2O$, t-butylchromate in $CCl_4$—AcOH—$Ac_2O$, $CrO_3$-Pyridine can also utilised to conduct oxidation step. Dry material obtained after oxidation showed 30-40% AKBA by HPLC analysis.

Higher grade AKBA is obtained from the acetylation mixture by chromatographic methodology. Solid supports such as one or more of silica gel, reversed phase silica, alumina, sephadex and toyopearl can be used in the process. Chromatographic techniques are selected from gravity column, flash chromatography, reversed phase chromatography, preparative high pressure liquid chromatography and the combinations thereof. Solvents such as acetone, chloroform, dichloromethane, ethyl acetate, hexane and water either alone or in combination to run a gravity column or flash column or medium pressure column are used.

This invention relates to a process for producing 10% to 100% of AKBA from an extract containing a mixture of boswellic acids, obtained from gum resin of *Boswellia* species, which comprises the steps of oxidising the said boswellic acids containing fraction and subsequent acetylation of said oxidised fraction, followed by chromatographic separation to obtain a fraction enriched in AKBA in the range of 30 to 100%. A fraction enriched in AKBA in the range of 10-30% can be accomplished by suitably diluting 40% enriched sample with a suitable excipient or natural boswellic acids mixture or by controlling the extent of oxidation by limiting the oxidant during the conversion process.

BEST METHOD OF CARRYING OUT THIS INVENTION

Figure 1:
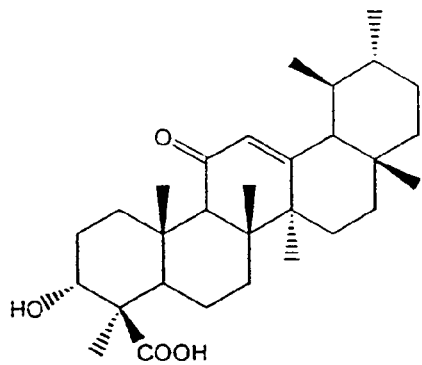
FIG. 1, shows the six boswellic acids present in an extract obtained from the gum resin.
Figure 1:
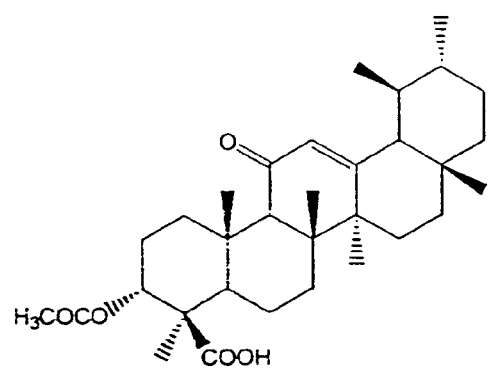
Figure 1:
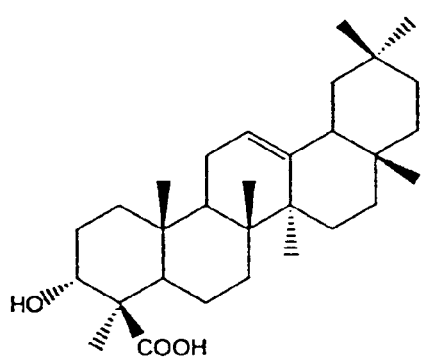
Figure 1:
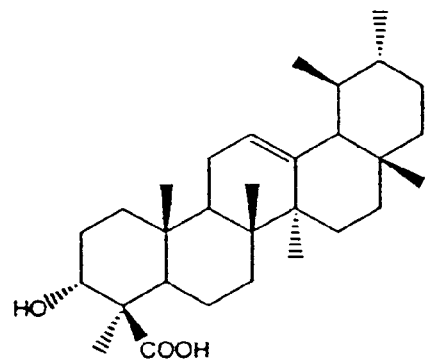
Figure 1:
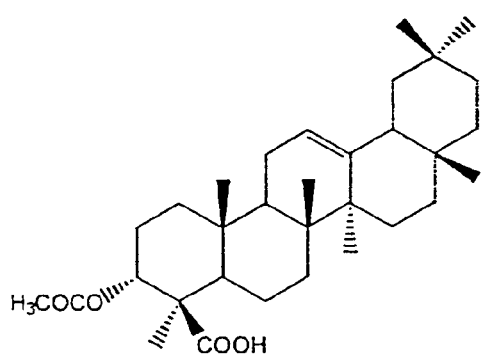
Figure 1:
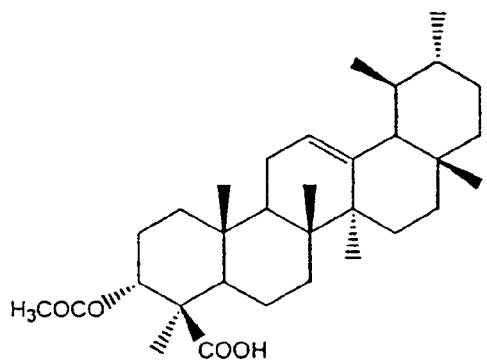
Figure 2:
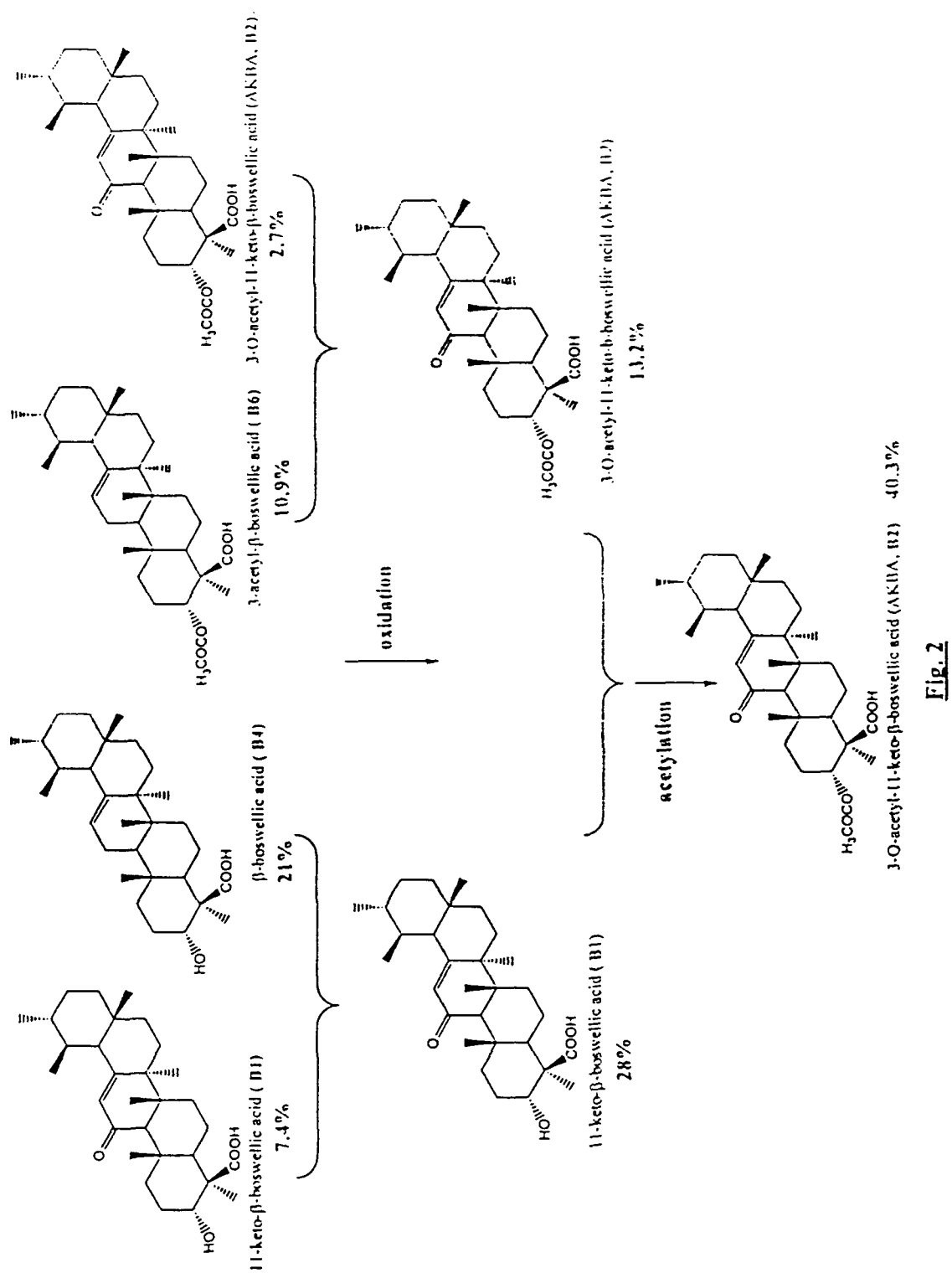
FIG. 2 is a flow chart showing the reaction scheme consisting of oxidation and acetylation resulting in 40.3% AKBA after conversion of the other β-boswellic acids into AKBA.

The following example illustrates one of the best methods of carrying out the process according to this invention.

Oxidation Step:

The boswellic acids mixture (85%, 20 g) containing 2.7% 3-O-acetyl-11-keto-β-boswellic acid was dissolved in 1.2 L of dioxane in a 2 L round bottom flask. N-Bromosuccinimide (24 g) was then added to the mixture. Calcium carbonate (20 g) was then added followed by 0.12 L of water. The reaction mixture was then stirred at room temperature. After 24 hours, the mixture was poured into crushed ice and extracted with 2×300 mL of ethyl acetate. The combined organic layer was successively washed with 200 mL of water and 200 mL of brine and dried over 50 g of sodium sulphate. The extract was evaporated and dried under vacuum to obtain 18.4 g of a mixture containing 28% of 11-keto-β-boswellic acid (B1) and 13.2% of 3-O-acetyl-11-keto-β-boswellic acid (B2).

Acetylation Step:

To a mixture of ketoboswellic acids (20 g), obtained in the oxidation step in 20 mL of dichloroethane, 12 mL of acetyl chloride, 10 mL of pyridine were added. The mixture was stirred at 60° C. for 3 h and at room temperature for 12 h. The reaction mixture was poured into crushed ice and stirring continued for about 10 min. White precipitate formed was filtered and washed thoroughly with distilled water and dried at 50° C. in a vacuum drier for three hours to obtain a mixture of boswellic acids as acetates (20.3 g). HPLC analysis showed that the mixture contained 40.3% of 3-O-acetyl-11-keto-β-boswellic acid (AKBA).

Further Enrichment of AKBA:

10 g of the above mixture of boswellic acid, which was assayed to contain 40.3% of AKBA was subjected to flash chromatography on a silica column using 200 mL of hexane, 200 mL of 8% ethyl acetate/hexane and 200 mL of 12% ethyl acetate in hexane as eluants. Each 20 ml fractions were collected. Fractions containing AKBA were combined and evaporated to obtain a residue of 4.0 g, which exhibited 80% of AKBA by HPLC analysis.

Enrichment of AKBA to 100%:

The 80% pure AKBA obtained in the previous step was subjected to repeated chromatography over silica gel using acetone and hexane mixtures as eluants to obtain 98 to 100% AKBA.

Alternately, 80% pure AKBA was subjected to preparative HPLC on C18 column (Phenomenex, Luna, 250 mm×21.2 mm, 10μ, $\lambda_{max}$ 248 nm, 20 mL/min) using acetonitrile and water mixtures as eluants to obtain 99-100% AKBA ($t_R$ 13 min).

Though the above example describes a specific embodiment of this invention, obvious equivalents and modifications known to persons skilled in the art are not excluded from the scope of the appended claims.

The invention claimed is:

1. A process for enriching 3-O-acetyl-11-keto-β-boswellic acid (AKBA) content in an extract containing a mixture of boswellic acids obtained from gum resin of *Boswellia* species, said extract containing 1% to 10% of AKBA, said process consisting essentially of the steps of oxidizing said extract followed by acetylation of the oxidized extract to obtain an AKBA-enriched extract having an AKBA content in the range of 30% to 40% by weight.

2. A process for enriching 3-O-acetyl-11-keto-β-boswellic acid (AKBA) content in an extract containing a mixture of boswellic acids obtained from gum resin of *Boswellia* species, said extract containing 1% to 10% by weight of AKBA, said process consisting essentially of the steps of acetylating the said extract followed by oxidizing the acetylated extract to obtain an AKBA-enriched extract having an AKBA content in the range of 30% to 40% by weight.

3. The process of claim 1, wherein said oxidation step is carried out by treating the extract with any one of the following, (i) selenium dioxide in ethanol or (ii) sodium dichromate in AcOH—$Ac_2O$ or (iii) t-butylchromate in $CCl_4$—AcOH—$Ac_2O$ or $CrO_3$-pyridine or (iv) N-bromosuccinimide-calcium carbonate in dioxane and water to obtain an oxidized extract.

4. The process of claim 1, wherein said acetylation step is carried out by treating the oxidized extract in dichloroethane with acetyl chloride in the presence of pyridine to obtain an enriched extract containing 30%-40% 3-O-acetyl-11-keto-β-boswellic acid.

5. The process of claim 2, wherein said acetylation step is carried out by treating said extract in dichloroethane with acetyl chloride in the presence of pyridine to obtain acetylated extract.

6. The process of claim 2, wherein said oxidation step is carried out by treating said acetylated extract with any one of the following (i) selenium dioxide in ethanol or (ii) sodium dichromate in AcOH—$Ac_2O$ or (iii) t-butylchromate in $CCl_4$—AcOH—$Ac_2O$ or $CrO_3$-pyridine or (iv) N-bromosuccinimide-calcium carbonate in dioxane and water to obtain an oxidized extract.

7. A process for enriching 3-O-acetyl-11-keto-β-boswellic acid (AKBA) content in an extract containing a mixture of boswellic acids obtained from gum resin of *Boswellia* species, said extract containing 1% to 10% of AKBA, said process consisting essentially of the steps of oxidizing said extract followed by acetylation of the oxidized extract to obtain an AKBA-enriched extract having an AKBA content in the range of 30% to 40% by weight; and subjecting said oxidized and acetylated extract to column chromatography over silica gel or reversed phase C8 silica or C18 silica or alumina or sephadex or toyopearl gel to obtain a fraction enriched up to 80% of 3-O-acetyl-11-keto-β-boswellic acid.

8. A process for enriching 3-O-acetyl-11-keto-β-boswellic acid (AKBA) content in an extract containing a mixture of boswellic acids obtained from gum resin of *Boswellia* species, said extract containing 1% to 10% by weight of AKBA, said process consisting essentially of the steps of acetylating the said extract followed by oxidizing the acetylated extract to obtain an AKBA-enriched extract having an AKBA content in the range of 30% to 40% by weight; and subjecting said oxidized and acetylated extract to column chromatography over silica gel or reversed phase C8 silica or C18 silica or alumina or sephadex or toyopearl gel to obtain a fraction enriched up to 80% of 3-O-acetyl-11-keto-β-boswellic acid.

9. The process of claim 7, wherein said column chromatography is carried out by eluting with acetone, chloroform, dichloromethane, ethyl acetate, hexane, methanol and water either alone or in combination.

10. The process of claim 8, wherein said column chromatography is carried out by eluting with acetone, chloroform, dichloromethane, ethyl acetate, hexane, methanol and water either alone or in combination.

11. An enriched extract containing 3-O-acetyl-11-keto-β-boswellic acid (AKBA) from an extract obtained from gum resin of *Boswellia* species having an AKBA content in the range of 30-40% by weight, wherein the said enriched extract is prepared by a process according to claim 1.

12. An enriched extract containing 3-O-acetyl-11-keto-β-boswellic acid (AKBA) from an extract obtained from gum resin of *Boswellia* species having an AKBA content in the range of 30-40% by weight, wherein the said enriched extract is prepared by a process according to claim 2.

13. An enriched extract containing 30% to 80% of 3-O-acetyl-11-keto-β-boswellic acid from an extract obtained from gum resin of *Boswellia* species, wherein the said enriched extract is prepared by a process according to claim 7.

14. An enriched extract containing 30% to 80% of 3-O-acetyl-11-keto-β-boswellic acid from an extract obtained from gum resin of *Boswellia* species, wherein the said enriched extract is prepared by a process according to claim 8.

15. A process for enriching 3-O-acetyl-11-keto-β-boswellic acid (AKBA) content in an extract containing a mixture of boswellic acids obtained from gum resin of *Boswellia* species, said extract containing 1% to 10% of AKBA, said process consisting essentially of the steps of oxidizing said extract followed by acetylation of the oxidized extract to obtain an AKBA-enriched extract having an AKBA content in the range of 30% to 40% by weight; and further followed by the step of enriching 3-O-acetyl-11-keto-β-boswellic acid (AKBA) content in the acetylated extract using column chromatography, to obtain an enriched extract containing up to 80% AKBA.

16. A process for enriching 3-O-acetyl-11-keto-β-boswellic acid (AKBA) content in an extract containing a mixture of boswellic acids obtained from gum resin of *Boswellia* species, said extract containing 1% to 10% by weight of AKBA, said process consisting essentially of the steps of acetylating the said extract followed by oxidizing the acetylated extract to obtain an AKBA-enriched extract having an AKBA content in the range of 30% to 40% by weight; and further followed by the step of enriching 3-O-acetyl-11-keto-β-boswellic acid (AKBA) content in the oxidized extract using column chromatography, to obtain an enriched extract containing up to 80% AKBA.

17. A process for enriching 3-O-acetyl-11-keto-β-boswellic acid (AKBA) content in an extract containing a mixture of boswellic acids obtained from gum resin of *Boswellia* species, said extract containing 1% to 10% of AKBA, said process comprising either:

a) oxidizing said extract containing a mixture of boswellic acids, followed by acetylating the oxidized extract, wherein no step of isolating a purified boswellic acid is conducted prior to said acetylating the oxidized extract; or b) acetylating said extract containing a mixture of boswellic acids, followed by oxidizing the acetylated extract, wherein no step of isolating a purified boswellic acid is conducted prior to said oxidizing the acetylated extract;

wherein steps (a) and (b) each produce an AKBA-enriched extract having an AKBA content in the range of 30% to 40% by weight.

\* \* \* \* \*